United States Patent [19]

D'Alelio

[11] 3,985,835

[45] Oct. 12, 1976

[54] HALOGENATED ESTERS OF PHOSPHORUS-CONTAINING ACIDS

[76] Inventor: Gaetano F. D'Alelio, 2011 E. Cedar St., South Bend, Ind. 46617

[22] Filed: Nov. 22, 1974

[21] Appl. No.: 526,229

Related U.S. Application Data

[60] Division of Ser. No. 383,513, July 30, 1973, Pat. No. 3,886,237, which is a continuation-in-part of Ser. No. 179,543, Sept. 10, 1971, Pat. No. 3,780,144, which is a continuation-in-part of Ser. No. 785,335, March 19, 1968, abandoned.

[52] U.S. Cl. .............................................. 260/956
[51] Int. Cl.² ........................................ C07F 9/24
[58] Field of Search .................................. 260/956

[56] References Cited
UNITED STATES PATENTS 2,574,517  11/1951  Walter et al. .................. 260/956 X

*Primary Examiner*—Anton H. Sutto
*Attorney, Agent, or Firm*—Walter J. Monacelli

[57] ABSTRACT

This invention deals with new phosphorus-containing esters having the formula
   R'''$_2$NP(O) (ORCX=CXR')$_2$
wherein X represents Cl or Br;
R represents a divalent hydrocarbon radical of 1–20 carbon atoms;
R' represents H, X or R'';
R'' represents a monovalent hydrocarbon radical of 1–20 carbon atoms;
R''' represents hydrogen, a monovalent hydrocarbon radical of 1–20 carbon atoms, a divalent saturated aliphatic hydrocarbon group having 5 carbon atoms between valencies and forming a cyclic structure with the N, or a derivative of said monovalent hydrocarbon radical in which the derivative group is hydroxy, NH$_2$, NHR'', NR''$_2$, -NR''''K, R''''NHNHC(O)-, R''''NHC(O)NH-,

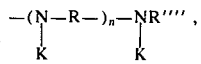

R''COO-, R''CONH- or R''O,
R'''' represents hydrogen or R'';
n represents an integer having a value of 0–50; and
K represents hydrogen, R'' or -P(O)(ORCX=CXR')$_2$. These new esters are useful particularly as fire retardants, agricultural chemicals, fuel additives, plasticizers, monomers and intermediates for the synthesis of other useful derivatives.

13 Claims, No Drawings

HALOGENATED ESTERS OF PHOSPHORUS-CONTAINING ACIDS

This application is a division of application Ser. No. 383,513, filed July 30, 1973, issued on May 27, 1975 as U.S. Pat. No. 3,886,237, which in turn is a continuation-in-part of application Ser. No. 179,543, filed Sept. 10, 1971, issued as U.S. Pat. No. 3,780,144 on Dec. 18, 1973, which in turn is a continuation-in-part of application Ser. No. 785,335, filed Dec. 19, 1968, now abandoned.

BACKGROUND OF THE INVENTION

1. Field of the Invention

This invention involves new esters containing both phosphorus and halogen atoms in their structures. More specifically, it concerns the phosphite esters of halogenated acetylenic alcohols. It also concerns derivatives of such esters obtained by the reaction of these esters with amines having hydrogen attached to the nitrogen thereof.

2. Related Prior Art

No pertinent prior art is known.

STATEMENT OF THE INVENTION

The esters of this invention are represented by the formula:

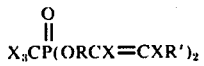

wherein
R represents a divalent hydrocarbon radical containing 1–20 carbon atoms;
R' represents X, hydrogen or R'';
R'' represents a monovalent hydrocarbon radical containing 1–20 carbon atoms; and
X represents chlorine or bromine.

The esters of this invention are prepared readily by the following reaction using one mole of phosphite reagent per mole of $CX_4$:

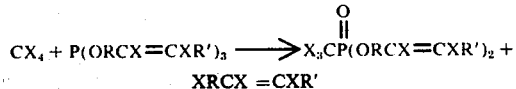

The byproduct XRCX=CXR' may be distilled from the reaction mass leaving the desired product as the residue.

The $X_3CP(O)(ORCX=CXR')_2$ may be reacted with ammonia or an amine having one or two hydrogen atoms attached to the nitrogen to liberate chloroform or bromoform and a phosphorus amide:

This same amide may be prepared directly by having the amine present during the reaction of the $CX_4$ and the original phosphite. In the above formulas R''' represents hydrogen, R'' and hydroxy and amine derivatives thereof. Where there are more than one amine group having hydrogen attached and sufficient of the phosphorus compound is used there will be a plurality of phosphorus amide groups in the resultant product.

The divalent hydrocarbon radical represented by R in the above formulas can be aliphatic, cycloaliphatic or aromatic and can be saturated or have ethylenic or acetylenic unsaturation therein. Aliphatic radicals include aryl-substituted aliphatic radicals such as phenylethylene, phenylenedimethylene, etc.; aromatic radicals include alkyl, alkenyl and alkynyl substituted aromatic radicals such as tolylene, xylylene, ethylphenylene, vinylphenylene, propargylphenylene, etc.; and cycloaliphatic radicals include alkyl, alkenyl, alkynyl and aryl substituted cycloaliphatic radicals such as ethylcyclohexylene, vinylcyclohexylene, propargylcyclohexylene, phenylcycloheptylene, tolylcyclopentylene, etc. The simpler and smaller of these radicals are preferred for obvious reasons, but the more complicated radicals can also be used and are included in the scope of this invention.

These divalent hydrocarbon radicals are illustrated by the following typical radicals: $-CH_2-$; $-(CH_2)_2-$; $-(CH_2)_4-$; $-(CH_2)_7-$; $-(CH_2)_{12}-$; $-C(CH_3)_2-$; $-CH(CH_3)-$; $-CH(C_6H_5)-$; $-CH(C_6H_{11})-$; $-CH(C_4H_9)-$; $-CH(C_8H_{17})-$; $-CH_2CH(C_6H_5CH_3)-$; $-CH(CH_3)CH_2CH_2-$; $-CH_2CH=CHCH_2-$; $-CH_2C\equiv CCH_2-$; $-CH_2CH(CH=CH_2)-$; $-CH(C\equiv CH)CH_2-$; $-CH(CH_2C_6H_5)CH_2-$; $-CH_2C_6H_4CH_2-$; $-CH_2CH_2C_6H_4-$; $-C_6H_4-$; $-C_6H_3(CH_3)-$; $-C_{10}H_6-$; $-C_{10}H_5(C_2H_5)-$; $-C_6H_3(CH=CH_2)-$; $-C_6H_3(CH_2C\equiv CH)-$; $-C_6H_4-C_6H_4-$; $-C_6H_4(C_6H_5)-$; $-C_6H_{10}-$; $-C_5H_8-$; $-C_7H_{12}-$; $-C_6H_9(CH_3)-$; $-C_6H_9(C_6H_5)-$; $-C_6H_9(CH=CH_2)-$; $-C_7H_{11}(CH_2C\equiv CH)-$; $-CH_2C_6H_{10}CH_2-$; $-CH_2CH_2C_6H_{10}-$; $-(CH_2)_8CH=CH(CH_2)_{10}-$; and the like.

The monovalent hydrocarbon radical represented by R'' in the above formulas can be aliphatic, cycloaliphatic or aromatic and can be saturated or have ethylenic or acetylenic unsaturation therein. Aliphatic radicals include aryl-substituted aliphatic radicals such as phenylethyl, diphenylethyl, benzyl, tolylethyl, etc.; aromatic radicals include alkyl, alkenyl, and alkynyl substituted aromatic radicals such as tolyl, xylyl, ethylphenyl, vinylphenyl, propargylphenyl, etc.; and cycloaliphatic radicals include alkyl, alkenyl, alkynyl and aryl substituted cycloaliphatic radicals such as ethylcyclohexyl, vinylcyclohexyl, propargylcyclohexyl, phenylcycloheptyl, tolylcyclopentyl, etc. The simpler and smaller of these radicals are preferred for obvious reasons, but the more complicated radicals can also be used and are included in the scope of this invention.

These monovalent hydrocarbon radicals are illustrated by the following typical radicals: $-CH_3$; $-C_2H_5$; $-C_4H_9$; $-CH=CH_2$; $-(CH_2)_7CH_3$; $-(CH_2)_{12}CH_3$; $-CH(CH_3)_2$; $-CH(C_6H_5)_2$; $-CH_2CH=CH_2$; $-CH_2C\equiv CH$; $-CH_2C_6H_{11}$; $-CH_2CH_2C_6H_5CH_3$; $-CH(CH_3)CH_2CH_3$; $-CH_2CH_2CH=CH_2$; $-CH(C\equiv CH)CH_3$; $-CH(CH_2C_6H_5)CH_3$; $-CH_2C_6H_4CH_3$; $-CH_2C_6H_5$; $-CH_2CH_2C_6H_5$; $-C_6H_5$; $-C_6H_4CH_3$; $-C_6H_3(CH_3)_2$; $-C_{10}H_7$; $-C_{10}H_6C_2H_5$; $-C_6H_4CH=CH_2$; $-C_6H_4CH_2C\equiv CH$; $-C_6H_4-C_6H_5$; $-C_6H_3(C_6H_5)_2$; $-C_6H_{11}$; $-C_5H_9$; $-C_7H_{13}$; $-C_6H_{10}CH_3$; $-C_6H_{10}C_6H_5$; $-C_6H_{10}CH=CH_2$; $-C_7H_{12}CH_2C\equiv CH$; $-CH_2C_6H_{10}CH_3$; $-CH_2CH_2C_6H_{11}$; $-(CH_2)_8CH=CH(CH_2)_9CH_3$; and the like.

As defined above the R''' on the amine compounds used in the phosphorus amide-forming reaction can be hydrogen, or an R'' group as defined and illustrated above, or a hydroxy or amine derivative of an R'' group. The amines can be mono and diamines with the various R'' groups as the single or double substituted groups, such as monomethyl, dimethyl, monoethyl, diethyl amines, etc. with the various other R'' groups.

The typical R'' groups are listed above and typical hydroxy and amino derivatives of these include the following: hydroxyalkylamines, such as monoethanol amine, diethanol amine, isopropanol amine, diisopropanol amine, n-propanol amine, di-n-propanol amine, butanol amines, hexanol amines, etc.; polyamines, such as ethylenediamine, methyl ethylenediamine, dimethyl ethylenediamine, trimethyl ethylenediamine, propylenediamine, methyl propylenediamine, dimethyl propylenediamine, diethyl propylenediamine, tetramethylene diamine, hexamethylene diamine, diethylene triamine, tetraethylene penta-amine, etc.; polyimines, such as polyethyleneimine, polypropyleneimine, polybutyleneimine, etc., (The number of nitrogen atoms in such polyamines and polyimines have no upper limit, but from a practical standpoint no particular advantage is gained in having more than 50 nitrogen atoms in such compounds.); further substituted derivatives of such hydroxy and amine derivatives such as carboxy, ether and amide derivatives, e.g. acetoxyethyl amine, bis(acetoxyethyl)amine, acetoxypropyl amine, benzoxyethyl amine, beta-aminoethoxyethyl acetate, beta-aminoethyl acrylate, beta-aminopropoxyethyl acrylate, ethyl(3-aminocaproate), methyl(4-aminohexoate), allyl(4-aminohexoate), propargyl(5-aminooctoate), etc., ethoxyethylamine, bis(ethoxyethyl)amine, propoxypropylamine, phenoxybutylamine, cyclohexoxyethylamine, etc., acetamidoethyl amine, propanoamidoethyl amine, butyroamidopropyl amine, benzoamidoethyl amine, bis(acetamidoethyl)amine, etc.; addition polymers of amines having polymerizable ethylenic groups attached thereto such as polyacrylates having amino-substituted ester and amide groups, i.e. poly(beta-aminoethylacrylate), poly(beta-aminoethylacrylamide), poly(beta-aminopropyl methacrylate), poly(para-aminophenyl acrylate), poly(para-aminophenyl acrylamide), poly(para-aminobenzyl acrylamide), etc., polyallylamine, polymeric vinyl-beta-aminoethyl ether, polymeric p-aminostyrene, polymeric(beta-aminoethyl)-styrene, polymeric (aminoethyl)-styrene, etc.; hydrazines, such as hydrazine, phenyl hydrazine, diphenyl hydrazine, ethyl hydrazine, butyl hydrazine, etc.; semicarbazides, such as phenyl semicarbazide, diphenyl semicarbazide, methyl semicarbazide, etc.; cyclic amines, such as piperidine, 4-methyl piperidine, 2-ethyl piperidine, morpholine, etc.; heterocyclic amines, such as aminopyridine, methylaminopyridine, etc.

Both of the above reactions are advantageously conducted in the temperature range of 0° to 100° C., preferably 50°–100° C. When groups are present having a strong tendency to polymerize, a polymerization inhibitor of the various well known types, such as t-butyl catechol, may advantageously be present.

The period requred to complete reaction varies according to the temperature used. For example 100° C. a substantial amount of reaction is effected within 10 minutes, whereas at least 30 minutes, preferably at least one hour, is desired to effect substantial reaction at 0° C. In most cases a period of 1–5 hours is used to insure complete reaction.

The (-ORCX=CXR') type of esters of this invention differ from the esters of halogenated saturated alcohols, for example (-OCH$_2$CHXCH$_2$X), in having much greater hydrolytic stability of the halogen atoms than the latter type of esters, which show a much greater tendency to lose halogen. This loss of halogen occurs under conditions of high humidity, thereby limiting the utility of the saturated compound.

The novel phosphorus-containing esters of this invention are self-extinguishing when ignited and thus are particularly useful as fire-retardant additives for a host of other material and compounds, particularly those of a resinous or polymeric nature, for example, when added to polymethyl methacrylate, polystyrene, cellulose acetate, cellulose butyrate, the polyesters, the polyurethanes, rubbers, nylon and others. They can also be used as fire-retardant impregnants for porous bodies, such as paper, wood, fiberboard, cork, etc.

As organic compounds containing phosphorus and halogen atoms they are useful also as agricultural chemicals in the fields of insecticides, herbicides, pesticides, etc., as well as gasoline additives to function as metal scavengers for anti-knock gasolines containing organo-lead, -boron, or metallo-organo-compounds. Particularly are they useful as chemical intermediates in the synthesis of a host of other useful derivatives. The halo compounds can be halogenated further at the ethylenic double bond to produce higher halogenated compounds which have even greater self-extinguishing properties than the dihalo compounds. They also add to olefinic double bonds of the unsaturated compounds to yield plasticizers as well as polymerizable monomers. They react with epoxy compounds to produce substituted alcohols which can be used as modifiers of urethane polymers, polyesters, cellulose, etc.

In addition to their flame retardant properties the compounds of this invention also find utility as agricultural chemicals and as fuel additives. In addition, when the parent compounds or derivatives contain functional groups, such as the OH groups, they can be used as modifiers in polymerization reactions or can be reacted with other functional molecules such as with the isocyanates, acid anhydrides, acid chlorides, oxirane compounds, etc., or when they contain an unsaturated olefinic group they can be homopolymerized or copolymerized with other monomers; or when they contain an amide group they can be reacted with aldehydes and polymerized alone or copolymerized with urea or melamine, or their methylol compounds can be reacted with cellulose or wool, etc.

The practice of this invention is illustrated by the following examples. These examples are given merely by way of illustration and are not intended to limit the scope of the invention in any way nor the manner in which the invention can be practiced. Unless specifically indicated otherwise, parts and percentages are given as parts and percentages by weight.

EXAMPLE I

One hundred forty-five parts (145) of 1,2,3-trichloropropane are added to a solution of 106 parts of sodium carbonate dissolved in 900 parts of water and the mixture refluxed for ten hours. The water layer is then separated from the oily layer which is dried over anhydrous sodium carbonate, separated by filtration and distilled. There is obtained 115 parts of 2,3-dichloro-2-propene-1-ol, ClCH=CClCH$_2$OH, (I), b.p. 45°–46° C./1.5 mm; yield 91%.

EXAMPLE II a. To 250 parts of carbon tetrachloride is added 56 parts of propargyl alcohol (A) and to this solution there is added slowly, at room temperature, a solution of 160 parts of bromine in 250 parts of carbon tetrachloride and allowed to react at room temperature for two hours. Then the mixture is heated to 30°–40° C. for two hours. The product is distilled to recover the carbon tetrachloride and the 2,3-dibromo-2-propene-1-ol, BrCH=CBrCH₂OH, (II), b.p. 51°–52° C./0.7 mm; yield 93%.

b. Treatment of 1,2,3-tribromopropene with aqueous sodium carbonate by the procedure of Example I yields the same 2,3-dibromo-2-propene 1-ol.

EXAMPLE III

The reaction of 2-methyl-3-butyn-2-ol (B) with NaOCl under an inert atmosphere of nitrogen according to the procedure given in the Bull. soc. chim. (France), p. 1615 (1965) gives an 87% yield of 4-chloro-2-methyl-3-butyl-2-ol,

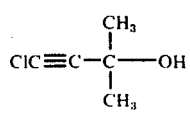
(III)

B.P. 54°–56° C./18 mm. This may be halogenated by the process of Example II to give the trihalo acetylenic alcohol Cl(Br)C=C(Br)C(CH₃)₂OH or by similarly chlorinating to give Cl₂C=C(Cl)C(CH₃)₂OH.

EXAMPLE IV

The reaction of 2-methyl-3-butyl-2-ol in water with Br₂ and NaOH by the procedure given in Ann. Chem. (Rome), 47, 118 (1957) yields 4-bromo-2-methyl-3-butyn-2-ol,

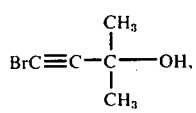
(IV), b.p. 92°–93° C./22 mm. This may be halogenated by the process of Example II to give the trihalo acetylenic alcohol Br₂C=C(Br)C(CH₃)₂OH.

EXAMPLE V

The procedure of Example II(a) is repeated using instead of propargyl alcohol, one equivalent weight of the following acetylenic alcohols to obtain the halo-derivative corresponding to the alcohol used:

| Acetylenic Alcohol | | Dibromoethylene Derivative | |
|---|---|---|---|
| HC≡C—CH(CH₃)—OH | (C) | HC=C(Br)—C(Br)(CH₃)H—OH | (V) |
| HC≡C—CH(C₂H₅)—OH | (D) | HC=C(Br)—C(Br)(C₂H₅)H—OH | (VI) |
| HC≡C—CH(C₃H₇)—OH | (E) | HC=C(Br)—C(Br)(C₃H₇)H—OH | (VII) |
| HC≡C—CH(C₄H₉)—OH | (F) | HC=C(Br)—C(Br)(C₄H₉)H—OH | (VIII) |
| HC≡C—CH(C₈H₁₇)—OH | (G) | HC=C(Br)—C(Br)(C₈H₁₇)H—OH | (IX) |
| HC≡C—CH(C₆H₅)—OH | (H) | HC=C(Br)—C(Br)(C₆H₅)H—OH | (X) |
| HC≡C—C(CH₃)₂—OH | (B) | HC=C(Br)—C(Br)(CH₃)₂—OH | (XI) |
| HC≡C—C(CH₃)(C₂H₅)—OH | (I) | HC=C(Br)—C(Br)(CH₃)(C₂H₅)—OH | (XII) |
| HC≡C—C(CH₃)(C₄H₉)—OH | (J) | HC=C(Br)—C(Br)(CH₃)(C₄H₉)—OH | (XIII) |
| HC≡C—C(C₄H₉)₂—OH | (K) | HC=C(Br)—C(Br)(C₄H₉)₂—OH | (XIV) |
| H₃C—C≡C—CH₂OH | (L) | CH₃C(Br)=C(Br)—CH₂OH | (XV) |
| H₃C—C≡C—CH₂CH₂OH | (M) | CH₃C(Br)=C(Br)—CH₂CH₂OH | (XVI) |

| Acetylenic Alcohol | | Dibromoethylene Derivative | |
|---|---|---|---|
| $C_6H_5C{\equiv}C{-}(CH_2)_{10}OH$ | (N) | $C_6H_5\underset{\underset{Br}{\mid}}{C}{=}\underset{\underset{Br}{\mid}}{C}{-}(CH_2)_{10}OH$ | (XVII) |
| $H_{41}C_{20}C{\equiv}C{-}CH_2OH$ | (O) | $H_{41}C_{20}\underset{\underset{Br}{\mid}}{C}{=}\underset{\underset{Br}{\mid}}{C}{-}CH_2OH$ | (XVIII) |
| $H_3CC{\equiv}C{-}CH_2\underset{\underset{CH_3}{\mid}}{C}H{-}OH$ | (P) | $H_3C\underset{\underset{Br}{\mid}}{C}{=}\underset{\underset{Br}{\mid}}{C}{-}CH_2\underset{\underset{CH_3}{\mid}}{C}H{-}OH$ | (XIX) |
| $C_4H_9C{\equiv}C{-}CH_2OH$ | (Q) | $C_4H_9\underset{\underset{Br}{\mid}}{C}{=}\underset{\underset{Br}{\mid}}{C}{-}CH_2OH$ | (XX) |
| $C_6H_5C{\equiv}C{-}CH_2OH$ | (R) | $C_6H_5\underset{\underset{Br}{\mid}}{C}{=}\underset{\underset{Br}{\mid}}{C}{-}CH_2OH$ | (XXI) |
| $C_6H_5C{\equiv}C{-}CH_2CH_2OH$ | (S) | $C_6H_5\underset{\underset{Br}{\mid}}{C}{=}\underset{\underset{Br}{\mid}}{C}{-}CH_2CH_2OH$ | (XXII) |
| $C_6H_{11}C{\equiv}C{-}CH_2OH$ | (T) | $C_6H_{11}\underset{\underset{Br}{\mid}}{C}{=}\underset{\underset{Br}{\mid}}{C}{-}CH_2OH$ | (XXIII) |
| $C_6H_5C{\equiv}C{-}\underset{\underset{CH_3}{\mid}}{C}H{-}OH$ | (U) | $C_6H_5\underset{\underset{Br}{\mid}}{C}{=}\underset{\underset{Br}{\mid}}{C}{-}\underset{\underset{CH_3}{\mid}}{C}H{-}OH$ | (XXIV) |
| $C_6H_5C{\equiv}C{-}\underset{\underset{CH_3}{\mid}}{\overset{\overset{CH_3}{\mid}}{C}}{-}OH$ | (V) | $C_6H_5\underset{\underset{Br}{\mid}}{C}{=}\underset{\underset{Br}{\mid}}{C}{-}\underset{\underset{CH_3}{\mid}}{\overset{\overset{CH_3}{\mid}}{C}}{-}OH$ | (XXV) |
| $ClC{\equiv}C{-}\underset{\underset{CH_3}{\mid}}{\overset{\overset{CH_3}{\mid}}{C}}{-}OH$ | (III) | $Cl\underset{\underset{Br}{\mid}}{C}{=}\underset{\underset{Br}{\mid}}{C}{-}\underset{\underset{CH_3}{\mid}}{\overset{\overset{CH_3}{\mid}}{C}}{-}OH$ | (XXVI) |
| $BrC{\equiv}C{-}\underset{\underset{CH_3}{\mid}}{\overset{\overset{CH_3}{\mid}}{C}}{-}OH$ | (IV) | $Br\underset{\underset{Br}{\mid}}{C}{=}\underset{\underset{Br}{\mid}}{C}{-}\underset{\underset{CH_3}{\mid}}{\overset{\overset{CH_3}{\mid}}{C}}{-}OH$ | (XXVII) |
| $C_{10}H_7C{\equiv}CCH_2OH$ | (W) | $C_{10}H_7\underset{\underset{Br}{\mid}}{C}{=}\underset{\underset{Br}{\mid}}{C}{-}CH_2OH$ | (XXVIII) |

EXAMPLE VI a. To a solution of 56 parts of propargyl alcohol and 0.1 part of iodine in 300 parts of tetrachloroethylene is slowly passed chlorine gas while exposed to an ultraviolet lamp until 70 parts of chlorine are reacted. The halogenated product is then recovered by distillation and the majority of the product is identical to the 2,3-dichloro-2-propene-1-ol of Example I.

b. In a similar manner there is prepared

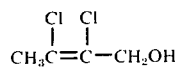  (XXIX).

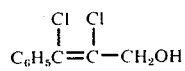  (XXX).

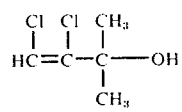  (XXXI)

and

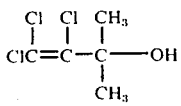  (XXXII).

The halogenated acetylenic alcohols prepared in the above examples may be used in preparing the $P(ORCX{=}CXR')_3$ and $HOP(ORCX{=}CXR')_2$ reagents used for preparing the new compositions of this invention as illustrated in some of the following examples.

EXAMPLE VII a. The phosphite ester,

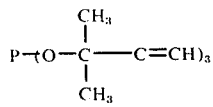

is prepared from $PCl_3$ and

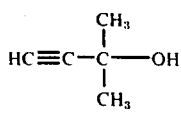
 (B)

by the procedure given in U.S. Pat. No. 2,278,791, Dec. 27, 1955, and converted by the procedure of Example II(a) by reaction with Br₂ to

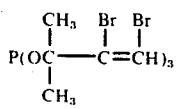

b. In a manner similar to the procedure of Example VII(a) the acetylenic alcohols III, IV, C, D, L and M are converted to the phosphite esters, P(ORC ≡ CR")₃, and by post bromination to esters corresponding to the formula

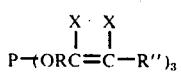

EXAMPLE VIII

A mixture of 46 parts of PCl₃, 126 parts of 2,3-dichloro-2-propene-1-ol and 150 parts of toluene is refluxed until no more HCl is evolved from the reaction. The mixture is then allowed to cool to room temperature; then 5 parts of anhydrous sodium carbonate and 3 parts of decolorizing carbon are added to the solution and allowed to stand with stirring for 8 to 24 hours. The solution is then filtered and the filtrate distilled at 0.5 to 14 mm Hg pressure to recover the toluene. The yield of almost colorless residue is 96% of the theoretical amount. The infrared spectra of the product confirm the absence of the band for the -OH group of the alcohol and the presence of the band for the ester group. The product is a viscous oil insoluble in water but soluble in benzene and toluene. The elemental analyses of the product: percent C, 26.95; percent H, 2.24; percent Cl, 52.56; are in close agreement with the theoretical values of C, 26.42; H, 2.20; Cl, 52.02 for P(OCH₂CCl=CHCl)₃. The boiling point of the product is higher than 120° C. at 0.5 mm Hg. Attempts to distill the product at higher pressures, or at higher temperatures at 0.5 mm pressure results in secondary reactions which change the nature of the product, which product, however, is still self-extinguishing. Other triesters of this type having other R groups in place of the -CH₂- and/or having bromine in place of the chlorine or having the tetrachloro or tetrabromo structure can be similarly prepared for use as intermediates in preparing phosphate esters of the present invention.

EXAMPLE IX a. An equimolar mixture of P(OCH₂CCl=CHCl)₃ and CCl₄ is heated in a closed reactor in a nitrogen atmosphere at 100° C. under autogenous pressure for 3 hours, following which the mixture is distilled to recover ClCH=CClCH₂Cl, leaving as a residue, the product

Analyses for C, H, O, Cl and P correspond closely to those of the above formula.

b. The procedure of (a) is repeated using an equivalent amount of CBr₄ in place of CCl₄ and Br₃CP(O)-(OCH₂CCl=CHCl)₂ is obtained as the product.

c. The procedures of (a) and (b) are repeated using an equivalent amount of P(OCH₂CBr=CHBr)₃ as the phosphorus-halogen reagent and the corresponding products are prepared:
Cl₃CP(O)(OCH₂CBr=CHBr)₂, and
Br₃CP(O)(OCH₂CBr=CHBr)₂, respectively.

d. By substituting equivalent amounts respectively of various other phosphorus-halogen reagents the following compounds are also prepared:

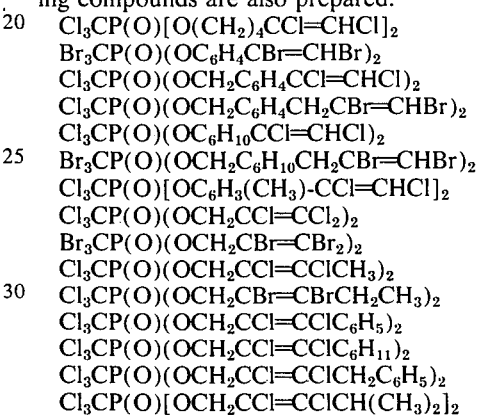

EXAMPLE X a. A number of reactions are performed in a closed reactor using one mole of Cl₃CP(O)-(OCH₂CCl=CHCl)₂ with one mole each of a number of nitrogen compounds containing at least one hydrogen atom attached to the nitrogen, namely: ammonia, methylamine, ethanolamine, diethanolamine, aniline, p-vinyl aniline, p-acryloxyaniline, p-acrylamidoaniline and (beta-acrylamido)ethylamine. Reaction at 100° C. for one hour liberates one mole of chloroform, CHCl₃, and gives H₂NP(O)(OCH₂CCl=CHCl)₂, H₃CHNP(O)-(OCH₂CCl=CHCl)₂, HOCH₂CH₂NHP(O)-(OCH₂CCl=CHCl)₂, (HOCH₂CH₂)₂NP(O)-(OCH₂CCl=CHCl)₂, C₆H₅NHP(O)-(OCH₂CCl=CHCl)₂, CH₂=CHC₆H₄NHP(O)-(OCH₂CCl=CHCl)₂, CH₂=CHCOOC₆H₄NHP(O)-(OCH₂CCl=CHCl)₂, CH₂=CHCONHC₆H₄NHP(O)-(OCH₂CCl=CHCl)₂ and CH₂=CHCONHCH₂CH₂NH-P(O)(OCH₂CCl=CHCl)₂ respectively. The identical products are obtained if one mole of P(OCH₂CCl=CHCl)₃, carbon tetrachloride and amine are reacted initially and directly. Analyses of these compounds for C, H, N, P and Cl are in close agreement with the theoretical values and confirm the structures.

b. When the above procedures are repeated using Br₃CP(O)(OCH₂CCl=CHCl)₂, bromoform is liberated in each case and the same phosphamide compounds are obtained as above.

c. The procedures of (a) are repeated using Cl₃CP(O)(OCH₂CBr=CHBr)₂ as the phosphorus-halogen reagent and the following compounds are prepared:

$H_2NP(O)(OCH_2CBr=CHBr)_2$
$CH_3NHP(O)(OCH_2CBr=CHBr)_2$
$HOCH_2CH_2NHP(O)(OCH_2CBr=CHBr)_2$
$(HOCH_2CH_2)_2NP(O)(OCH_2CBr=CHBr)_2$
$C_6H_5NHP(O)(OCH_2CBr=CHBr)_2$
$CH_2=CHC_6H_4NHP(O)(OCH_2CBr=CHBr)_2$
$CH_2=CHCOOC_6H_4NHP(O)(OCH_2CBr=CHBr)_2$
$CH_2=CHCONHC_6H_4NHP(O)(OCH_2CBr=CHBr)_2$
$CH_2=CHCONHCH_2CH_2NHP(O)-(OCH_2CBr=CHBr)_2$

EXAMPLE XI

The procedure of Example X is repeated a number of times using one mole each time of $HOCH_2CH_2NH_2$ and one mole each respectively of the compounds prepared in Example IX(d) and the following compounds are prepared:
$HOCH_2CH_2NHP(O)[O(CH_2)_4CCl=CHCl]_2$
$HOCH_2CH_2NHP(O)(OC_6H_4CBr=CHBr)_2$
$HOCH_2CH_2NHP(O)(OCH_2C_6H_4CCl=CHCl)_2$
$HOCH_2CH_2NHP(O)(OCH_2C_6H_4CH_2CBr=CHBr)_2$
$HOCH_2CH_2NHP(O)(OC_6H_{10}CCl=CHCl)_2$
$HOCH_2CH_2NHP(O)(OCH_2C_6H_{10}CH_2CBr=CHBr)_2$
$HOCH_2CH_2NHP(O)[OC_6H_3(CH_3)CCl=CHCl]_2$
$HOCH_2CH_2NHP(O)(OCH_2CCl=CCl_2)_2$
$HOCH_2CH_2NHP(O)(OCH_2CBr=CBr_2)_2$
$HOCH_2CH_2NHP(O)(OCH_2CCl=CClCH_3)_2$
$HOCH_2CH_2NHP(O)(OCH_2CBrCH_2CH_3)_2$
$HOCH_2CH_2NHP(O)(OCH_2CClC_6H_5)_2$
$HOCH_2CH_2NHP(O)(OCH_2CCl=CClC_6H_{11})_2$
$HOCH_2CH_2NHP(O)(OCH_2CCl=CClCH_2C_6H_5)_2$
$HOCH_2CH_2NHP(O)[OCH_2CCl=CClCH(CH_3)_2]_2$ by reaction with acrylyl chloride each of these compounds is converted to a polymerizable derivative and when homopolymerized or copolymerized with benzoyl peroxide according to the conditions described below in Example XV, polymers are obtained with very good self-extinguishing properties.

EXAMPLE XII

Samples of the various phosphorus esters of Examples IX through XI are placed individually in a microcrucible and in each case the contents ignited by the flame of a microburner. When the flame is withdrawn in each case burning stops completely.

EXAMPLE XIII

Ten parts of $Cl_3CP(O)(OCH_2CCl=CHCl)_2$ are added respectively to each of the following, which are approximately 50% solvents and 50% solids, (a) a clear alkyd varnish, (b) a cellulose acetate-butyrate lacquer, (c) a white-pigment oil-modified epoxy paint, and (d) a pigmented urethane-type paint; then films are cast from the mixtures and allowed to dry or cure for four days. Attempts to ignite the resulting films showed in each case that they are self-extinguishing. Similar results are obtained when the other esters selected from Examples IX through XI are similarly tested.

EXAMPLE XIV

A skein of 20 parts of cotton thread is placed in 500 parts of an aqueous solution containing 2.5 parts NaOH, 2.5 parts $CS_2$ and 0.05 parts of sodium dodecylbenzene sulfonate and allowed to stand for 30 minutes. The thread is then removed, washed thorougly with distilled water, and immersed in 500 parts of a solution containing 0.05 parts of $FeSO_4\cdot(NH_4)_2SO_4$ and 1.5 parts of tetra-bis-hydroxymethyl phosphonium chloride for ten minutes. The thread is then washed with distilled water and suspended in 1000 parts of an emulsion containing 8 parts of $CH_2=CHC_6H_4NHP(O)-(OCH_2CBr=CHBr)_2$, 0.1 parts of sodium dodecylbenzene sulfonate and 1.5 parts of hydrogen peroxide and the mixture heated with agitation under nitrogen for 3 hours. The thread is then removed, washed with water and dried. There is obtained 28 parts of greafted thread, which when suspended and its end ignited, is self-extinguishing when the source of the flame is withdrawn.

EXAMPLE XV

A mixture of 50 parts $CH_2=CHC_6H_4NHP(O)-(OCH_2CBr=CHBr)_2$, 50 parts toluene and 0.5 parts of benzoyl peroxide is polymerized in a sealed container under nitrogen and at 80° C. for 10 hours. The toluene is evaporated to give a solid resin. Five parts of this is mixed with 100 parts respectively of polystyrene, polymethyl methacrylate, polyacrylonitrile, polybutadiene, polyvinylacetate and molded in each case to a hard casting. In each case attempts to ignite each casting shows the product to be self-extinguishing. The procedure is repeated with $CH_2=CHCOOC_6H_4NHP(O)-(OCH_2CCl=CHCl)_2$, $CH_2=CHCONHC_6H_4NHP(O)-(OCH_2CCl=CHCl)_2$, $CH_2=CHCONHCH_2CH_2NH-P(O)(OCH_2CCl=CHCl)_2$ and $CH_2=CHCONHCH_2CH_2-NHP(O)(OCH_2CBr=CHBr)_2$, and in each case the product is found to be self-extinguishing.

EXAMPLE XVI

The procedure of Example X(a) is repeated a number of times using individually and in the amount indicated (per mole of the phosphorus-chloro compound) the following nitrogen compounds:

a. ½ mole hydrazine
b. 1 mole phenylhydrazine
c. ½ mole semicarbazide
d. 1 mole 1-phenylsemicarbazide
e. 1 mole 4-phenylsemicarbazide
f. ½ mole ethylenediamine
g. ½ mole tetramethyl diamine
h. 1/6 mole tetraethylene hexamine The respective products have the following formulas:

a. $[-NHP(O)(OCH_2CCl=CHCl)_2]_2$
b. $C_6H_5NHNHP(O)(OCH_2CCl=CHCl)_2$ c. 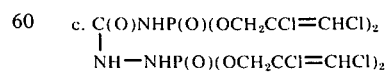
$\begin{array}{l}C(O)NHP(O)(OCH_2CCl=CHCl)_2 \\ | \\ NH-NHP(O)(OCH_2CCl=CHCl)_2\end{array}$ d. $C_6H_5NHC(O)NHNHP(O)(OCH_2CCl=CHCl)_2$
e. $C_6H_5NHNHC(O)NHP(O)(OCH_2CCl=CHCl)_2$
f. $[-CH_2NHP(O)(OCH_2CCl=CHCl)_2]_2$
g. $[-CH_2CH_2NHP(O)(OCH_2CCl=OHCl)_2]_2$ h. 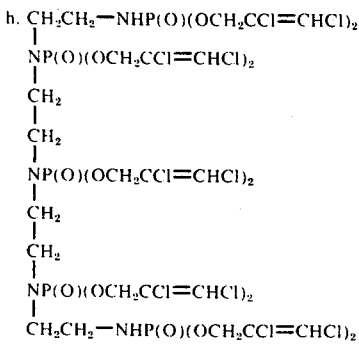

When tested according to the procedures of Examples XII and XIII each of the above products is found to have similar self-extinguishing characteristics.

EXAMPLE XVII

The procedure of Example X(a) is repeated a number of times using $CH_2=CHC_6H_4CH_2NH_2$ as the amine compound to give a class of compounds having the general formula $CH_2=CHC_6H_4CH_2NHP(O)(ORCX=CXR')_2$ by using the following phosphorus halogen starting compounds to obtain the indicated products:

a. $Cl_3CP(O)(OCH_2CCl=CHCl)_2 \rightarrow CH_2=CHC_6H_4CH_2NHP(O)(OCH_2CCl=CHCl)_2$
b. $Cl_3CP(O)(OCH_2CBr=CHBr)_2 \rightarrow CH_2=CHC_6H_4CH_2NHP(O)(OCH_2CBr=CHBr)_2$
c. $Cl_3CP(O)(OCH_2CCl=CCl_2)_2 \rightarrow CH_2=CHC_6H_4CH_2NHP(O)(OCH_2CCl=CCl_2)_2$
d. $Cl_3CP(O)(OCH_2CBr=CBr_2)_2 \rightarrow CH_2=CHC_6H_4CH_2NHP(O)(OCH_2CBr=CBr_2)_2$
e. $Cl_3CP(O)(OCH_2CH_2Cl=CHCl)_2 \rightarrow CH_2=CHC_6H_4CH_2NHP(O)(OCH_2CH_2CCl=CHCl)_2$
f. $Cl_3CP(O)(OC_6H_4CBr=CHBr)_2 \rightarrow CH_2=CHC_6H_4CH_2NHP(O)(OC_6H_4CBr=CHBr)_2$ Each of the products is tested according to the procedures of Examples XII–XV and in each case shows fire-extinguishing properties.

As shown above the phosphorus-containing esters of this invention having polymerizable ethylenic groups therein are polymerizable by themselves or in mixtures with each other or in mixtures with other vinyl or vinylidene monomers, sometimes referred to herein as vinyl monomers, such as styrenes, i.e., styrene, alphamethylstyrene, vinyl naphthalene, vinyl diphenyl, etc., with acrylates, such as methyl acrylate, methyl methacrylate, butyl acrylate, ethyl chloracrylate, etc., vinyl esters such as vinyl acetate, vinyl benzoate, vinyl butyrate, etc., acrylonitrile, methacrylonitrile, esters of polymerizable dibasic acids such as dimethyl maleate, diethyl fumarate, diallyl phthalate, divinyl azelate, dimethyl itaconate, etc., maleic anhydride, itaconic anhydride, etc.

In producing self-extinguishing copolymers with such copolymerizing monomers, such properties are exhibited with as little as 0.1 percent by weight, preferably at least 1 percent by weight, of a monomer of this invention. In blends of homopolymers or copolymers of these phosphorus-containing esters with other polymers, such as polystyrene, etc., there is advantageously at least 0.1 percent, preferably at least 1 percent by weight, of the product represented by the phosphorus-containing ester portion.

In polymerizing such polymerizable esters of this invention the various polymerization systems and techniques known in the art may be used, such as free-radical, e.g. peroxy and azo systems, thermal, radiation and various other systems. For most purposes for which the polymer products are to be used molecular weights of at least 500, preferably at least 1,000, are desirable.

While certain features of this invention have been described in detail with respect to the various embodiments thereof, it will, of course, be apparent that other modifications may be made within the spirit and scope of this invention, and it is not intended to limit the invention to the exact details shown above except insofar as they are defined in the following claims:

The invention claimed is:

1. A phosphorus-halogen-nitrogen-containing compound having the formula $$R'''_2NP(O)(ORCX=CXR')_2$$

wherein

X represents Cl or Br;
R represents a divalent hydrocarbon radical of 1–20 carbon atoms;
R' represents H, X or R'';
R'' represents a monovalent hydrocarbon radical of 1–20 carbon atoms; and
R''' represents hydrogen or a monovalent hydrocarbon radical of 1–20 carbon atoms.

2. A compound of claim 1 in which X is Cl.
3. A compound of claim 1 in which X is Br.
4. A compound of claim 1 in which R is $CH_2$.
5. A compound of claim 4 in which both R''' groups represent hydrogen.
6. A compound of claim 4 in which one R''' group represents hydrogen and one represents $CH_3$.
7. A compound of claim 1 having the formula $C_6H_5NHP(O)(OCH_2CX=CHX)_2$.
8. A compound of claim 1 having the formula $CH_2=CHC_6H_4NHP(O)(OCH_2CX=CHX)_2$.
9. A compound of claim 1 having the formula $CH_2=CHC_6H_4CH_2NHP(O)(ORCX=CXR')_2$.
10. A compound of claim 9 having the formula $CH_2=CHC_6H_4CH_2NHP(O)(OCH_2CCl=CHCl)_2$.
11. A compound of claim 9 having the formula $CH_2=CHC_6H_4CH_2NHP(O)(OCH_2CBr=CHBr)_2$.
12. A compound of claim 9 having the formula $CH_2=CHC_6H_4CH_2NHP(O)(OCH_2CCl=CCl_2)_2$.
13. A compound of claim 9 having the formula $CH_2=CHC_6H_4CH_2NHP(O)(OCH_2CBr=CBr_2)_2$.

* * * * *